US012551200B2

(12) United States Patent
Beyers et al.

(10) Patent No.: US 12,551,200 B2
(45) Date of Patent: Feb. 17, 2026

(54) SMALL VOLUME LIQUID SAMPLER

(71) Applicant: Novosanis NV, Wijnegem (BE)

(72) Inventors: Koen Catharina Lodewijk Beyers, Wuustwezel (BE); Alejandra Ríos Cortés, Kortenberg (BE); Nette Meers, Lier (BE); Christof Irma Jozeph Baks, Wommrlgem (BE); Quinten Van Avondt, Lier (BE); Timothi Julio Steven Van Mulder, Schilde (BE); Vanessa Vicky Jill Vankerckhoven, Wilrijk (BE)

(73) Assignee: Novosanis NV, Wijnegem (BE)

(*) Notice: Subject to any disclaimer, the term of this patent is extended or adjusted under 35 U.S.C. 154(b) by 583 days.

(21) Appl. No.: 17/767,252

(22) PCT Filed: Oct. 7, 2020

(86) PCT No.: PCT/EP2020/078023
§ 371 (c)(1),
(2) Date: Apr. 7, 2022

(87) PCT Pub. No.: WO2021/069454
PCT Pub. Date: Apr. 15, 2021

(65) Prior Publication Data

US 2022/0370047 A1 Nov. 24, 2022

Related U.S. Application Data

(60) Provisional application No. 62/911,817, filed on Oct. 7, 2019.

(51) Int. Cl.
*A61B 10/00* (2006.01)
*A61F 5/44* (2006.01)

(52) U.S. Cl.
CPC .......... *A61B 10/007* (2013.01); *A61F 5/4405* (2013.01)

(58) Field of Classification Search
CPC .... A61B 10/007; A61F 5/4405; G01N 1/2042
See application file for complete search history.

(56) References Cited

U.S. PATENT DOCUMENTS 3,894,845 A 7/1975 McDonald
4,305,405 A 12/1981 Meisch
(Continued)

FOREIGN PATENT DOCUMENTS

CN 1420750 A 5/2003
CN 101583316 A 11/2009
(Continued)

OTHER PUBLICATIONS

Office Action for Chinese Patent Application No. 202080083706.2, dated Feb. 25, 2025, 8 pages.
(Continued)

*Primary Examiner* — Catherine T. Rastovski
*Assistant Examiner* — Brian Butler Geiss
(74) *Attorney, Agent, or Firm* — Lippes Mathias LLP

(57) ABSTRACT

A device for sampling an initial volume of a liquid flow is disclosed which comprises an inlet conduit, an outlet conduit, and valve casing. The valve casing has a passageway formed therethrough. A sample outlet extends through the valve casing and into the passageway. A valve structure is arranged for axial movement in the valve casing. A gate of the valve structure obstructs the passageway and prevents an initial volume of the liquid flow from being transferred to the outlet conduit when the valve structure is moved to a sampling position. A stem of the valve structure obstructs the sample outlet without obstructing the passageway when the valve structure is moved to a diverting position. At least one
(Continued)

elongated groove is formed in a surface of the gate and extends into the stem such that the initial volume is directed through the sample outlet and towards a receptacle when the valve structure is moved to the sampling position. A lifting member moves the valve structure from the sampling position to the diverting position.

20 Claims, 4 Drawing Sheets

(56) References Cited

U.S. PATENT DOCUMENTS

| | | | | |
|---|---|---|---|---|
| 4,494,581 | A * | 1/1985 | Gordon | A61B 10/007 210/531 |
| 5,105,824 | A | 4/1992 | Rasch | |
| 5,275,042 | A | 1/1994 | Carson et al. | |
| 5,622,183 | A | 4/1997 | Hazard et al. | |
| 5,785,044 | A | 7/1998 | Meador et al. | |
| 7,435,242 | B2 | 10/2008 | Levinson | |
| 7,819,821 | B2 | 10/2010 | Forte et al. | |
| 8,328,733 | B2 | 12/2012 | Forte et al. | |
| 9,968,336 | B2 | 5/2018 | Van Damme et al. | |
| 2003/0149408 | A1 | 8/2003 | Levinson | |
| 2007/0074761 | A1 | 4/2007 | Salomon | |
| 2008/0228106 | A1 | 9/2008 | Forte et al. | |
| 2009/0048568 | A1 | 2/2009 | Levinson | |
| 2011/0040272 | A1 | 2/2011 | Forte et al. | |
| 2011/0237977 | A1* | 9/2011 | Knight | A61B 10/007 600/573 |
| 2011/0284220 | A1 | 11/2011 | Hayworth | |
| 2015/0223784 | A1 | 8/2015 | Van Damme et al. | |
| 2016/0022249 | A1 | 1/2016 | Forte | |
| 2016/0145659 | A1 | 5/2016 | Anderson et al. | |

FOREIGN PATENT DOCUMENTS

| | | | |
|---|---|---|---|
| CN | 102725209 | A | 10/2012 |
| CN | 102892688 | A | 1/2013 |
| CN | 104684489 | A | 6/2015 |
| CN | 205228869 | U | 5/2016 |
| DE | 1903251 | A1 | 8/1970 |
| DE | 2327699 | A1 | 12/1973 |
| GB | 1574864 | A | 9/1980 |
| JP | S6479658 | A | 3/1989 |
| JP | 2016514261 | A | 5/2016 |
| KR | 101876699 | B1 | 8/2018 |
| WO | 2004010873 | A1 | 2/2004 |
| WO | 2004043264 | A1 | 5/2004 |
| WO | 2005003725 | A2 | 1/2005 |
| WO | 2005107602 | A1 | 11/2005 |
| WO | 2008065325 | A1 | 6/2008 |
| WO | 2011042752 | A1 | 4/2011 |
| WO | 2011128607 | A1 | 10/2011 |
| WO | 2011140600 | A1 | 11/2011 |
| WO | 2014037152 | A1 | 3/2014 |
| WO | 2018191534 | A1 | 10/2018 |

OTHER PUBLICATIONS

Search Report for Chinese Patent Application No. 202080083706.2, dated Feb. 23, 2025, 3 pages.

Office Action for Australian Patent Application No. 2020364849, dated Mar. 31, 2025, 4 pages.

Office Action for Brazilian Patent Application No. 112022006712-7, dated Mar. 28, 2025, 7 pages.

Office Action for Singapore Patent Application No. 11202203610X, dated May 27, 2025, 4 pages.

Office Action for European Patent Application No. 20796701.9, dated Jul. 7, 2023, 5 pages.

Office Action for Japanese Patent Application No. 2022-521611, dated Jun. 11, 2024, 6 pages.

Office Action for Mexican Patent Application No. MX/a/2022/004214, dated May 6, 2025, 6 pages.

* cited by examiner

SMALL VOLUME LIQUID SAMPLER

CROSS-REFERENCE TO RELATED APPLICATIONS

This application is a National Stage Entry of International Application No. PCT/EP2020/078023, filed Oct. 7, 2020, and also claims the priority benefit of U.S. Provisional Application No. 62/911,817, filed Oct. 7, 2019, the disclosures of which are incorporated by reference herein in their entireties.

FIELD OF THE INVENTION

The present invention relates to the field of fluid volume sampling devices, and in particular to devices for sampling small initial volumes of a liquid flow.

BACKGROUND OF THE INVENTION

With the development of highly sensitive nucleic acid amplification testing of pathogenic DNA, self-collected first-void urine has become a valuable non-invasive sample for diagnostic purposes, for instance for the detection of urogenital infections such as *Chlamydia trachomatis*, as well as other sexually transmitted infections. Results of this testing method, however, are only conclusive if the sampled urine fraction is not diluted or contaminated by the subsequent mid-stream urine. Moreover, even within the first-void volume of urine, there are variations of the microorganism load in urine samples which depend on the precise initial volume sampled, e.g. only a small fraction of the first-void urine. Therefore, a need for liquid sampling devices exists which allow the precise sampling of an initial volume of a liquid flow, e.g. urine, and which are hygienic and comfortable in their use.

WO2014/037152 relates to a liquid sampling device for capturing a first portion of a liquid flow. The device comprises an inlet, an outlet, and a guide with a displaceable element which, in a first position, is capturing a first portion of the liquid flow, e.g. the first-void urine, into a reservoir, and which, in a second position, is blocking the access to the reservoir and is passing subsequent liquid to the outlet instead. The displaceable element moves in transverse direction to the liquid flow and has lifting means. Although being suitable for the sampling of first-void urine, it remains challenging for this device to restrict the quantity of sampled first-void urine to a small initial volume fraction thereof.

SUMMARY OF THE INVENTION

Miniaturizing buoyancy-driven liquid sampling devices described in WO2014/037152 A1 to make them fit to smaller volumes as required for diagnostics is challenging because the buoyancy force necessary to elevate the displaceable element (e.g. a valve) is strongly reduced for smaller-sized lifting means, such as air pockets or floaters, which still fit into the sampling receptacles. Another problem faced by miniaturization is the limited wall thickness that is yet obtainable by injection molding techniques, e.g. limited to 0.5 mm. There are indeed chances that designs with limited use of material, thus very thin-walled designs, with a wall thickness below 0.5 mm, e.g. 0.4 mm thick or thinner, are facing filling issues in the mold when they are injection molded. Further, the redirection of the sampled liquid volume through tubular ducts of small diameter is slow and possibly dominated by capillary action, which can result in liquid rapidly accumulating in the chamber (e.g. guide portion) connected between the inlet and outlet conduits. As liquid is held back and rises in the chamber, the inflow of the initial fraction is hampered and retarded. Ultimately, the subsequent volume may dilute or mix or contaminate with the initial volume to be sampled if the latter is not drained fast enough.

It is therefore an object of embodiments of the present invention to provide a device for sampling an initial volume of a liquid flow, hygienic and comfortable in use, which is also adapted for reliably sampling small initial volumes, e.g. volumes smaller than 20 ml, e.g. about 5 ml or less.

The above objective is accomplished by a device and a kit of parts according embodiments of to the present invention.

In one aspect the invention relates to a device for sampling an initial volume of a liquid flow and the device comprises an inlet conduit for receiving the liquid flow, an outlet conduit for draining a subsequent volume of the liquid flow, and a valve casing arranged between the inlet conduit and the outlet conduit. The valve casing has a passageway formed therethrough to fluidly connect the inlet conduit to the outlet conduit, for instance is providing an inlet and an outlet through a projecting sidewall. A sample outlet for draining the initial volume of the liquid flow is extending through the valve casing and into said passageway. Further, a valve structure is arranged for axial movement in the valve casing, traverse to a direction of liquid flow through the passageway. The valve structure comprises a gate for obstructing the passageway and for preventing the initial volume of the liquid flow from being transferred to the outlet conduit when the valve structure is in, e.g. moved to, a sampling position. Besides, the valve structure comprises a stem which is connected to the gate and adapted for obstructing the sample outlet without obstructing the passageway when the valve structure is in, e.g. moved to, a diverting position. At least one elongated groove is formed in a surface of the gate that faces the inlet conduit. The at least one groove extends from the gate into the stem such that the initial volume of the liquid flow is directed through the sample outlet and towards a receptacle, which is connectable to the valve casing, when the valve structure is in, e.g. moved to, the sampling position. The at least one elongated groove forms a narrow channel in the gate and the stem, which is fit to receive the inflowing initial volume and to guide it in a downward movement along the gate and the stem, and through the sample outlet if the valve structure is moved to the sampling position. The at least one elongated groove thus enables a liquid passageway for the initial volume flow between the inlet conduit and the sample outlet when the valve structure is in the sampling position. Moreover, a lifting member is connected to the stem for moving the valve structure from the sampling position to the diverting position while the initial volume of the liquid flow is being sampled through the sample outlet.

According to some embodiments of the present invention, the gate includes a slanted wall for achieving obstruction of the passageway through the valve casing and for obtaining an additional lifting force at the same time.

In some embodiments of the present invention, a resilient stopper is protruding from the inner surface of the valve casing to prevent a vertical displacement of the valve structure beyond the diverting position. Various height positions of the stopper can be determined to match a predetermined initial volume that is sampled in standardized receptacles, e.g. test tubes.

In some embodiments of the present invention, the rim of the cap and/or the outer edge of a lower portion of the stem is fitted (e.g. complementary in size and shape) to lie flush with a corresponding surface of the valve casing and the bore of the sample outlet respectively. This provides an efficient sealing effect.

In some embodiments of the present invention, the cap and/or ribbed edges of the valve structure are in a telescopic relationship with the inner surface of the valve casing and the bore of the sample outlet respectively. This improves a sliding axial movement of the valve structure relative to the valve casing by a guiding assistance at reduced friction.

According to some embodiments of the present invention, the cap has an asymmetrical shape (e.g. defined by its rim) to prevent a rotation movement of the valve structure around its axis of translation. Hereto, the valve structure may have a mating asymmetrical shape.

It is an advantage of embodiments of the present invention that the device can cope with a wide range of volumetric flow rates, including volumetric flow rates typical for urination, e.g. ranging from 1 ml/sec to 55 ml/sec.

It is an advantage of embodiments of the present invention that components of the device may be composed of biodegradable polymers or other suitable biomaterials, which can be readily disposed of after use.

It is an advantage of embodiments of the present invention that inlet conduits and/or funnels can be adapted for use by a specific gender. This increases user comfort and also reduces the risk of spillage.

It is an advantage of embodiments of the present invention that the components of the sampling device can be manufactured separately and assembled later. Hence, the components of the sampling device can be sent to the user as a kit of parts, involving only little shipment costs and the user can take samples at home.

In a further aspect the invention relates to a kit of parts, for assembling a device according to embodiments of the first aspect, which comprises a bonnet with at least three openings, an inlet conduit that is connectable to a first opening of the bonnet, an outlet conduit that is connectable to a second opening of the bonnet, and a valve casing that is removably insertable into the bonnet via a third opening therein. A base of the valve casing is connectable to the third opening, and the valve casing has an inlet and an outlet formed therethrough, defining a liquid passageway though the valve casing. A sample outlet extends through the base of the valve casing and into the passageway. Additionally, the valve casing has an opening provided at a top side, opposite to the base through which a valve structure is insertable. A valve structure, also included in the kit, is removably insertable into the valve casing. The valve structure is arranged for axial movement in the valve casing, traverse to a direction of liquid flow through the passageway. A gate of the valve structure is configured for obstructing the passageway when the valve structure is in, e.g. moved to, a sampling position, a stem of the valve structure is connected to the gate and adapted for obstructing the sample outlet without obstructing the passageway when the valve structure is in, e.g. moved to, a diverting position. At least one elongated groove is formed in a surface of the gate and extends into the stem. Moreover, the kit includes a lifting member that is connectable to the stem.

Alternatively, a kit of parts comprises a valve casing with an inlet and an outlet formed therethrough, defining a liquid passageway through the valve casing. The kit further comprises a sample outlet which extends through a base of the valve casing and into the passageway, and an inlet conduit and outlet conduit which are connectable to the inlet and the outlet of the valve casing respectively. An opening is provided at a top side of the valve casing, opposite to the base. Besides, a valve structure is included in the kit which is removably insertable into the valve casing. The valve structure is arranged for axial movement in the valve casing, traverse to a direction of liquid flow through the passageway. A gate of the valve structure is adapted for obstructing the passageway when the valve structure is in, e.g. moved to, a sampling position, and a stem of the valve structure is connected to the gate and adapted for obstructing the sample outlet without obstructing the passageway when the valve structure is in, e.g. moved to, a diverting position. At least one elongated groove is formed in a surface of the gate and extends from the gate into the stem. Furthermore, the kit comprises a lifting member that is connectable to the stem.

Particular and preferred aspects of the invention are set out in the accompanying independent and dependent claims. Features from the dependent claims may be combined with features of the independent claims and with features of other dependent claims as appropriate and not merely as explicitly set out in the claims.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The above and other aspects of the invention will be apparent from and elucidated with reference to the embodiment(s) described hereinafter.

BRIEF DESCRIPTION OF THE DRAWINGS

The invention will now be described further, by way of example, with reference to the accompanying drawings, in which.

Figure 1:
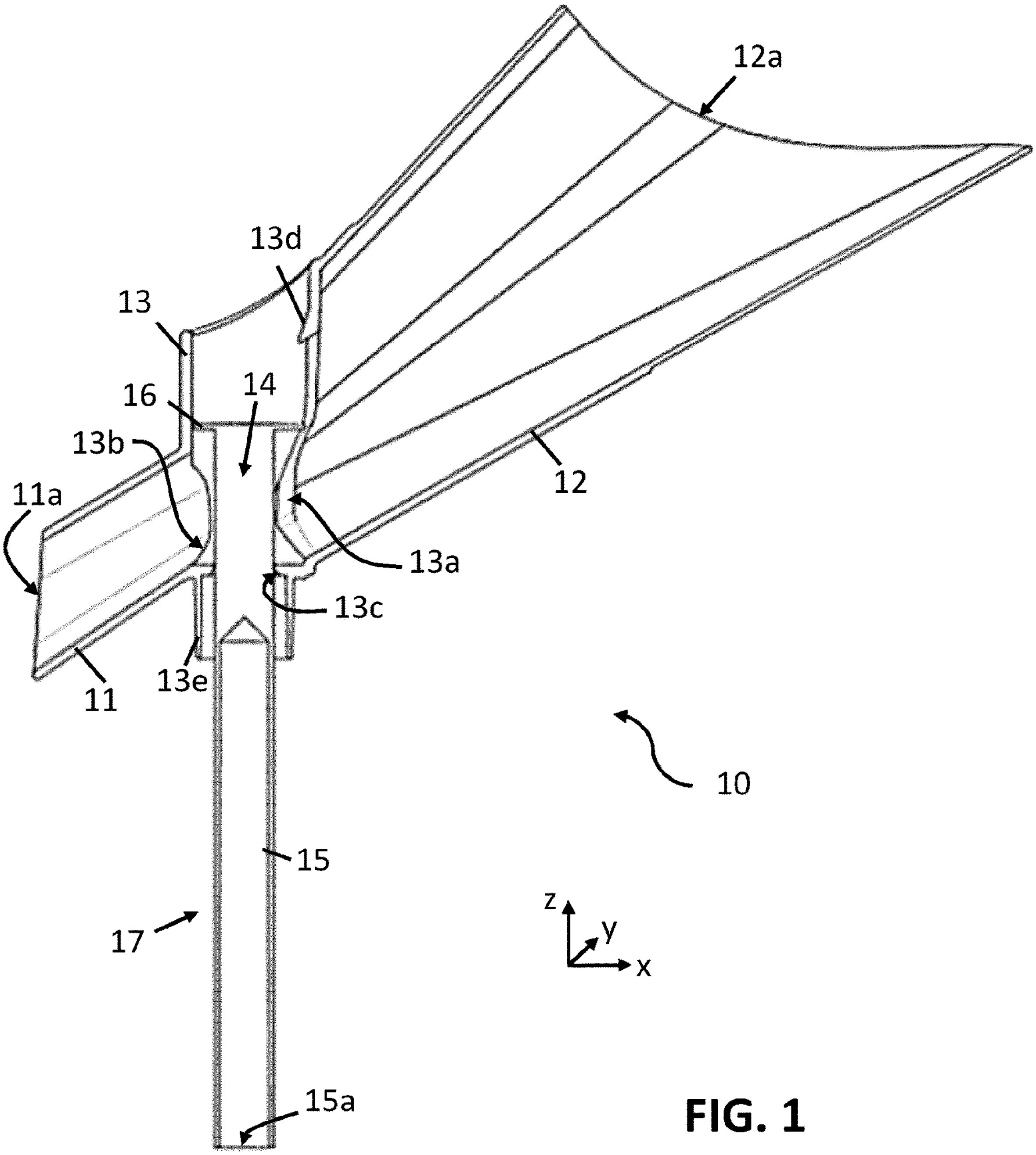
FIG. 1 is a cross-sectional view of a device for sampling an initial volume of a liquid flow according to an embodiment of the invention.

In the drawings, the size of some of the elements may be exaggerated and not drawn on scale for illustrative purposes. The dimensions and the relative dimensions do not necessarily correspond to actual reductions to practice of the invention.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims.

Moreover, directional terminology such as top, bottom, front, back, leading, trailing, under, over and the like in the description and the claims is used for descriptive purposes with reference to the orientation of the drawings being described, and not necessarily for describing relative positions. Because components of embodiments of the present invention can be positioned in a number of different orientations, the directional terminology is used for purposes of illustration only, and is in no way intended to be limiting, unless otherwise indicated. It is, hence, to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

It should be noted that the use of particular terminology when describing certain features or aspects of the invention should not be taken to imply that the terminology is being re-defined herein to be restricted to include any specific characteristics of the features or aspects of the invention with which that terminology is associated.

In the description provided herein, numerous specific details are set forth. However, it is understood that embodiments of the invention may be practiced without these specific details. In other instances, well-known methods, structures and techniques have not been shown in detail in order not to obscure an understanding of this description.

When reference is made in embodiments of the invention to a first-void volume of urine, this generally designates the first 20 ml to 50 ml of the initial urine flush. Small volumes in this respect, refer to volumes of first-void volume which are smaller than 20 ml, e.g. less than 10 ml, e.g. less than 5 ml, such as for instance 4 ml.

With reference to FIG. 1 to FIG. 5 of the drawings, a device for sampling an initial volume of a liquid flow (consisting of an initial volume and a subsequent volume) according to an embodiment of the invention is now described. FIG. 1 shows a cross-sectional view of the device 10, in which the section is taken in a mirror plane of the device perpendicular to the y-axis. The device 10 comprises an inlet conduit 12, an outlet conduit 11, a valve casing 13 and a valve structure 17. The valve structure 17 is inserted into the valve casing 13 and arranged to move axially inside the valve casing 13 between a sampling position and a diverting position. The inlet conduit 12 is adapted for receiving a liquid flow, e.g. urine, at a distant opening 12*a* and for guiding it towards the valve casing 13 and the outlet conduit 11 is adapted for draining the subsequent volume of the liquid flow, e.g. urine, away from the valve casing 13 and for expelling it from the device 10 at a distant opening 11*a*. Although the inlet conduit 12 and the opening 12*a* can be shaped in numerous ways, an inlet conduit 12 forming a funnel is preferred for the purpose of collecting the liquid efficiently and without spillage; particularly for the sampling of urine, the funnel-shaped inlet conduit 12 with a widened receiving lip as opening 12*a* offers the user a more hygienic and more comfortable use of the device 10. Moreover, the inlet conduit 12 and the outlet conduit 11 are preferably arranged at a slanting position with respect to a vertical z-axis along which the elongated valve structure 17 is typically aligned when the device 10 is operated, e.g. at angles ranging between 20 arc degrees and 70 arc degrees, e.g. about 45 arc degrees. This has the advantage that a liquid flow which enters the device 10 at the opening 12*a* at a low flow velocity is forced onward without delay, whereby a faster sampling of the initial volume thereof is achieved while contamination and sticking of the liquid to the inlet conduit 12 walls is prevented. Similarly, the removal of the subsequent volume of the received liquid flow from the valve casing 13 is accelerated by the slanted outlet conduit 11, thereby reducing the risk of contaminating the sampled initial volume by residuals of the subsequent volume remaining in the valve casing 13. The valve casing 13 has an inlet 13*a* and an outlet 13*b* formed therethrough, e.g. formed as openings in a projecting wall (in the z-direction) of the valve casing, a flat base supporting the projecting wall at a lower side, and an opening at an upper side, which opening is adapted for receiving the valve structure 17. A passageway for the liquid extends between the inlet 13*a* and the outlet 13*b* and through the hollow interior of the valve casing 13, wherein the inlet 13*a* and the outlet 13*b* are permanently aligned with proximate openings of the inlet conduit 12 and the outlet conduit 11 respectively. The proximate openings of the inlet conduit 12 and the outlet conduit 11 may be of equal shape and size as the inlet 13*a*, respectively the outlet 13*b* of the valve casing 13, or may be shaped differently and/or differ in size. In this particular embodiment, this permanent alignment is achieved by providing the inlet conduit 12, the outlet conduit 11, and the valve casing 13 as a single, monolithically formed unit, in which the inlet conduit 12 as well as the outlet conduit 11 are directly connected to the projecting wall of the valve casing 13. However, this way of connecting the inlet and outlet conduits 12, 11 to the valve casing 13 is not limiting and other connection means may be provided instead. For instance, a snap-fit connection may be made between plastic pieces, or push-in fittings or compression fittings may be used to connect the valve casing 13 to soft or hard tubing used for the inlet and outlet conduits 12, 11. A different connection scheme between valve casing 13 and inlet and outlet conduits 12, 11 is described further below with reference to FIG. 7 in relation to an alternative embodiment. A sample outlet 13*c*, e.g. a circular opening, is formed through the valve casing 13 at the flat base thereof and is leading into the passageway between the inlet 13*a* and outlet 13*b*.

The valve structure 17, as shown in FIG. 1, is in an inserted configuration, in which at least a gate 14 of the valve structure 17 is received inside the valve casing 13, e.g. in the hollow interior defined by the projecting walls, and an elongated stem 15 of the valve structure 17 is extending through the sample outlet 13*c*. Besides, the valve structure 17 is arranged for an axial movement in the valve casing 13 from a sampling position to a diverting position. For the embodiment described in reference to FIG. 1, the axial movement corresponds to a linear movement along the vertical direction (e.g. z-axis) and in a direction traverse to the direction of flow through the passageway between inlet 13*a* and outlet 13*b*, e.g. in a direction substantially perpendicular to the direction of flow through the passageway. Notwithstanding the preferred ninety degree angle between the axial movement of the valve structure 17 and the direction of flow through the passageway (e.g. defined by an inclination angle of the flat base of the valve casing about the z-axis), embodiments of the invention are not limited to ninety degree angle or angles close to the ninety degree angle. For instance, the flow direction for an inclined base may be slanted and the resulting angle between the flow direction through the passageway and the axial movement of the valve structure 17 may take values in the range (90+/−25) arc degrees. In this particular embodiment, a lifting member 15*a* is provided as an air-filled elongated cavity formed in the lower portion of the stem 15 and extending in the direction of axial movement of the valve structure 17, e.g. in the vertical z-direction. However, different embodiments of the invention may be provided with a different lifting member, for instance a block connected to an end portion of the stem or a block fastened to the stem and surrounding the same, which block comprises one or more air pockets, air-filled cavities, or comprises a porous material, e.g. a foam (e.g. an extruded polystyrene foam).

The sampling position, which is illustrated in FIG. 1, is adopted if the gate 14 is contacting the base of the valve casing 13 and a farther downward movement of the valve structure 17 with respect to the stationary valve casing 13 is prevented. More specifically, the valve structure is moved to the sampling position if a laterally outwards extending portion of a bottom edge of the gate 14 is physically contacting an upper side of the base in a region that is not overlapping the sample outlet 13*c*, e.g. the base portion surrounding the sample outlet 13*c* is acting as a seat for the gate 14. Moved to the sampling position, the gate 14 of the valve structure 17 is obstructing the liquid flow of the initial volume through the passageway between the inlet 13*a* and the outlet 13*b*.

Figure 2:
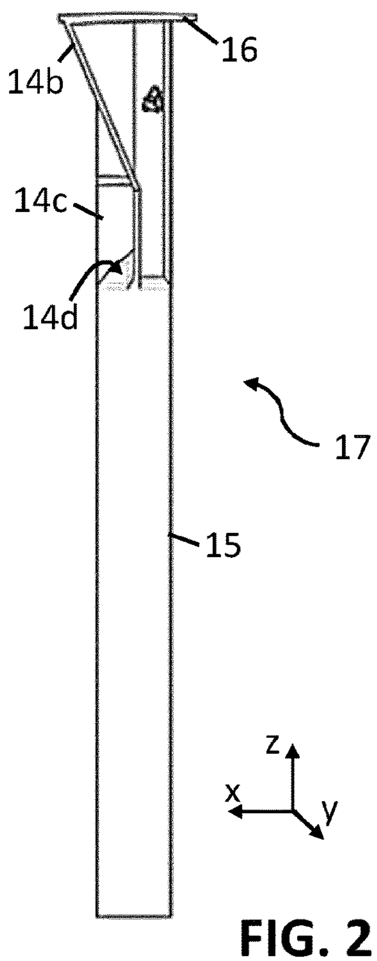
FIG. 2 and FIG. 3 are side and front elevation views of a valve structure as used in an embodiment of the invention.
Figure 3:
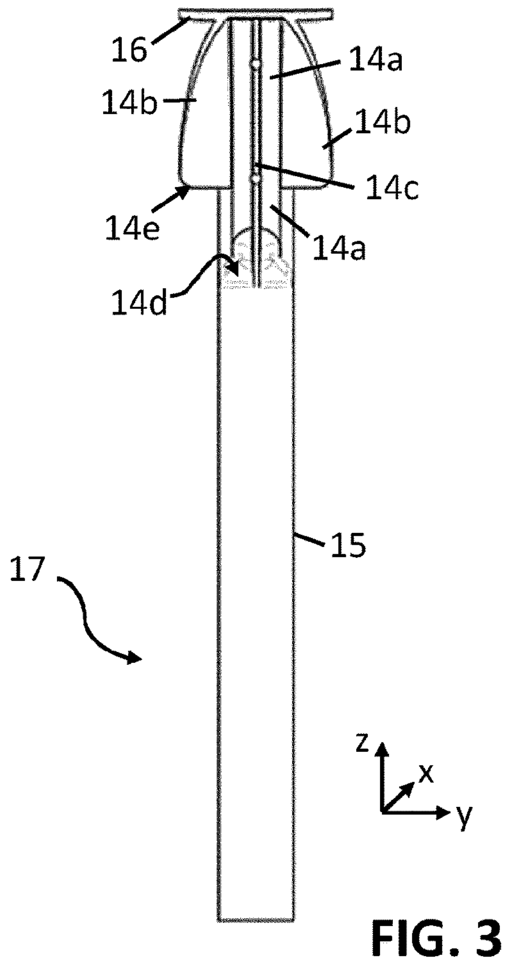
Figure 4:
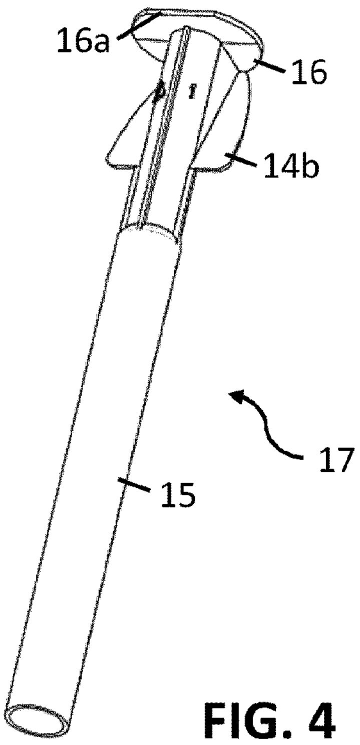
FIG. 4 and FIG. 5 are perspective views for the valve structure shown in FIG. 2 and FIG. 3.
Figure 5:
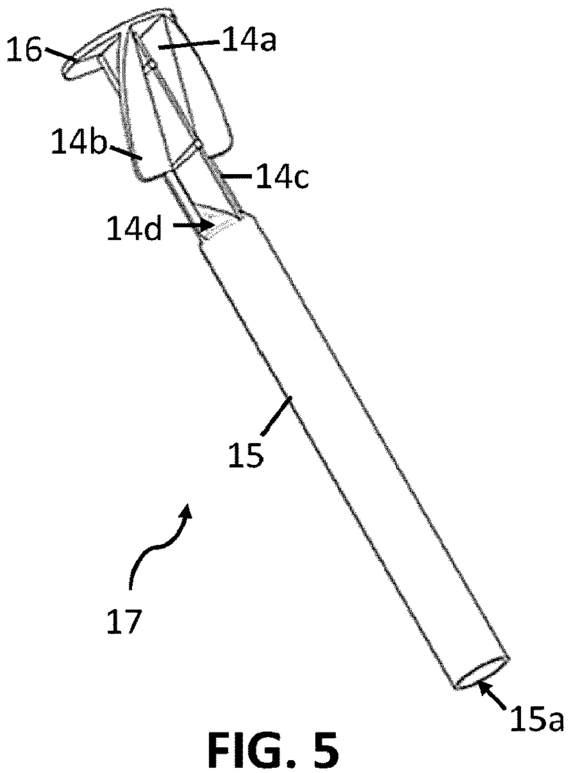

This obstruction mechanism of the gate 14 of the valve structure in the sampling position can be more readily understood by referring to FIG. 2 and FIG. 3, which are more detailed side elevation and front elevation views of the valve structure 17 respectively. In particular, the skilled person's attention is drawn to the presence of a slanted wall 14*b* of the gate 14 at a frontal side thereof. The wall 14*b* laterally extends, in the shape of two winged pieces, from a wedge-tapered central shaft, which is a continuation of the stem 15 in an upward direction. The slope angle of the wall 14*b* may be determined as the angle of intersection between a first plane that contains the base of the valve casing and a second plane, intersecting the first plane, which contains the diameter in y-directions across the sample outlet 13*c* in the base and the apex (in z-direction) of the arced curve defining the contour of the inlet 13*a*. A bottom edge 14*e* of the wall 14*b* joins the central shaft in the upper, thinned portion of the stem 15, above a beveled (e.g. conical) transition segment 14*d*, and the top edge of the wall is delimited by a flat cap 16. The wall 14*b* may have a spade-like contour and resemble a corresponding spade-like contour of a beaked inlet 13*a* of the valve casing 13. In particular, the projected contour of the wall 14*b* preferably covers the contour of the inlet 13*a* when projected onto a frontal plane. Furthermore, the contour of the wall 14*b* may be defined by the curve obtained by cutting a cylinder (e.g. for a cylindrical valve casing) with the second plane mentioned above. At least one groove 14*a* is formed in the surface of the wall 14*b* and extends towards and into the surface of the central shaft in the upper, thinned portion of the stem 15. The at least one groove 14*a* is more easily distinguished in the perspective view of the valve structure in FIG. 5. As shown in FIG. 2, FIG. 3 and FIG. 5, the at least one groove 14*a* may be considered as two separate grooves in the presence of a thin upwards raising, second wall 14*c*, which divides the groove space into two halves. This additional separating wall 14*c* has the advantage of increasing the structural integrity of the valve structure 17. The numerous details presented for the valve structure 17, help elucidating the obstruction mechanism for the gate 14 of the valve structure in the sampling position inside the valve casing 13. When the gate 14 is moved to the sampling position, the bottom edge 14*e* of the wall 14*b* are contacting the upper side of the valve casing base and the lateral winged edges of the wall 14*b* lie flush with the inner surface of the projecting wall of the valve casing 13, thereby providing the passageway through the valve casing with a sealing effect relative to the initial volume of the liquid flow. Moreover, the rim of the valve structure 17 is provided by the outwards directed edge of the cap 16. It is an advantage of embodiments of the invention that the cross-section of the cap 16 (in planar view, perpendicular to the z-axis) can be fitted to match, in shape and size, the inner boundary of the valve casing projecting wall such that the axial movement of the valve structure relative to the stationary valve casing is assisted and guided by the cap, e.g. the inner surface of the projecting wall of the valve casing 13 and the cap 16 are in a telescoping relationship. It is noted that the mentioned guiding aspect can be further improved by fitting the outer diameter of the stem in y-direction to the inner diameter of the sample outlet 13 in the same direction, which then also exhibit a telescoping relationship for their edges at least in the y-direction. As a result of the improved guiding of the valve structure 17 at two different heights (in z-direction), a tilting movement of the valve structure 17 can be prevented while still be able to move axially. In addition thereto, the so fitted cap 16 provides enhanced sealing of the passageway in respect of the initial volume of the received liquid flow, but also in respect to splashes or spilling of the subsequent volume of the received liquid flow, e.g. urine, when it is directed through the passageway to be expelled at the outlet conduit opening 11*a*. The skilled artisan knows, by design routine or trial and error, how to select appropriate clearances between the cap and the inner surface of the projecting wall, between the contours of the wall 14*b* and the inner surface of the projecting wall, as well as between the stem and the sample outlet, such that the guiding is performed without significant friction and yet amenable to sealing off the passageway.

As mentioned, the initial volume is prevented from entering the outlet conduit 11, hence well-preserved for sampling, if the valve structure 17 is moved to the sampling position and the passageway between the inlet 13*a* and the outlet 13*b* of the valve casing is blocked. However, there exists a fluid connection between the inlet 13*a* and the sample outlet 13*c* as long as the initial volume of the liquid flow is received and sampled. More specifically, the at least one groove 14*a* formed in the wall 14*b* of the gate 14 ensures that the received initial volume is redirected towards the sample outlet 13*c*. Because the at least one groove 14*a* (e.g. one single groove or two grooves separated by a wall 14*c*) extends downwards beyond the bottom edge 14*a* of the wall 14*b* and into the upper, thinned portion of the stem 15, the redirected flow of the initial volume indeed traverses the sample outlet 13*c* and continuous flowing downwards along the outer surface of the stem 15. This is facilitated by the smooth beveled transition segment 14*d* of the stem 15, which avoids that the redirected flow of the initial volume is projected back into the valve casing 13 if the transaction to the lower, wider portion of the stem 15 was too abrupt. In consequence, also a reaction force encumbering the swift lifting of the valve structure 17 to the diverting position to ensure a small sample volume is significantly reduced. Moreover, the slanted wall 14*b* also contributes to the redirection of the flow of the initial volume towards the base of the valve casing 13, where the redirected flow can still be drained through the sample outlet 13*c* owing to the thinned portion of the stem 15, e.g. the thinned cross-sectional area of the upper portion of the stem, between the transition segment 14*d* and the bottom edge 14*e* of the wall 14*b*, compared to the wider cross-sectional area of the lower portion of the stem 15 (as seen in planar view, perpendicular to the z-axis). A further advantage of the slanted wall 14*b* is given by the fact that the received initial volume of the liquid flow is exerting a (dynamic) pressure force on the wall 15*b* that is decomposed into a force component parallel to the flow direction and a force component parallel to the z-axis, e.g. the slanted wall 14*b* can be used to further enhance an upwards directed lifting force, in addition to the buoyancy force through the lifting member 15*a*, which is driving the valve structure 17 from the sampling position to the diverting position. This secondary lifting force by the slanted wall 14*b* is much appreciated in cases of small sampled initial volumes, e.g. about 4 ml of first-void urine, for which a volume of the lifting member that is submerged in the already sampled and collected liquid is typically small, hence achieving only small buoyancy forces, as volumes of collecting receptacles cannot be made arbitrarily small. Receptacles of too small volume will otherwise render capillary adhesion forces decisive and the initial volume is not removed quickly enough to prevent contamination thereof by the subsequent volume, e.g. contamination of an earlier fraction of the first-void urine by a later fraction of first-void or mid-stream urine.

Preferably, a tubular sampling connector 13*e* extends downwards from a lower side of the base of the valve casing 13, at least partially circumferentially enclosing the opening of the sample outlet 13*c*. A receptacle for collecting the initial volume of the sampled liquid flow, may be removably connectable to said sampling connector 13*e*, e.g. via a snap-fit or screw-fit connection. Gravitational acceleration forces assist in draining the initial volume through the sample outlet 13*c*, along the outer surface of the stem 15, and towards the receptacle that is connected to the sampling device 10 prior to use. It is advantageous to provide the sampling connector 13*e* with a recess over a portion of its circumference to obtain a sampling connector with a baffle-type end portion since this further assists and accelerates the draining process of the initial volume from the lower end of the groove 14*a* over the beveled transition segment 14*d* towards the outer surface of the lower portion of the stem 15, whereby the risk of sticking and congestion by accumulation of the drained liquid is reduced.

During use of the device 10, the liquid flow pertaining to the initial volume is sampled through the sample outlet 13*c* and generates a liquid column in a receptacle that has been previously connected to the device 10, e.g. to the sampling connector 13*e*. Preferably, the shape and depth of the receptacle is selected to cooperate with the lifting member 15*a* in that the formation of the liquid column in the receptacle is accompanied by a quickly progressing immersion of the lifting member 15*a*. The lifting member 15*a* may be provided as an air-filled cavity that is arranged in the hollow interior of the lower portion of the stem 15. This has the additional advantage that material weight and cost related to the formation of the elongated stem 15 is conveniently saved by provision of the cheap, low density fluid air. This also allows connectable receptacles of smaller diameter to be used to efficiently increase the immersed volume of the lifting member 15*a*, hence to increase the buoyancy force. Nevertheless, embodiments of the invention are not limited thereto and other floating structures and/or materials may be used instead of, or in addition to, air cavities in the lower portion of the stem 15, for instance a block of foams into which the lower end portion of the stem extends. As a consequence of the buoyancy force acting on the lifting member 15*a* as a floater, the valve structure 17 as a whole is lifted and forced upwards as the height of the sampled liquid column continues raising. The buoyancy-driven vertical displacement is stopped, and a further elevation of the valve structure 17 prevented, as soon as the diverting position is adopted.

In the diverting position, the upper side of the cap 16 is pushed up against a resilient stopper 13*d*, a projection protruding from the inner surface of the valve casing 13, e.g. a small flexible pin or stud extending inwards into the valve casing bore. The cap 16 is provided as a asymmetrically shaped disk, e.g. an originally circular disk of which a segment has been removed along a chord, which is most visible in the perspective view of FIG. 4. Hence, the rim of the cap 16 is lying flush with the inner side of the projecting walls of the valve casing 13 in the sampling position, in the diverting position, and in all the positions along the axial movement of the valve structure 17, whereby a sealing and guiding effect are obtained. Moreover, the asymmetrical shapes of the cap 16 and the bore of the valve casing 13 (e.g. the hollow interior defined by the projecting walls) are adapted to prevent a rotation movement around the vertical axis of displacement. Other shapes for the cap and the bore can be selected to yield the same effect, e.g. elliptical shape, polygonal shape, etc. The resilient stopper 13*d* is formed at a height (in z-direction) which corresponds to the buoyancy-driven elevation of the valve structure 17 when the initial volume has been drained through the sample outlet 13*c*. For high volume flow rates of the liquid to be sampled particularly, the sample outlet 13*c* aperture size and/or slanted wall 14*b* assist in obtaining a swift transition of the valve structure 17 from the sampling position to the diverting position, whereby the subsequent volume of the liquid flow is effectively prevented from passing through the sample outlet 13*c* and from contaminating the initial volume sample. It is further noticed that the thinned portion of the stem connected between the bottom edge 14*e* of the gate wall(s) 14*b* and the transition segment 14*d*, and the reduced lateral dimension in y-direction in particular (cf. FIG. 3), permits the subsequent volume of the liquid flow to be diverted through the passageway of the valve casing 13, between the inlet and outlet 13*a*, 13*b*. The gate 14 of the valve structure 17 being elevated in the diverting position, the obstruction of the passageway has been lifted. Moved to the diverting position, the valve structure 17 is also adapted to shut off the fluid connection between the inlet 13*a* and the sample outlet 13*c*. The transition segment 14*d* allows a smooth flow of the subsequent volume around the thinned portion of the stem and, at the same time, ensures that the thicker, lower portion of the stem 15 provides a plug to the sample outlet 13*c*. That is to say, the outer surface of lower portion of the stem 15 and the bore of the sample outlet 13*c* are fitted in size and shape to lie flush in the diverting position, thereby closing the sample outlet 13*c*. The skilled person is aware that a small clearance is needed and permissible to move the valve structure 17 back into the sampling position after the liquid flow has ceased and the sampled initial volume securely removed.

The outlet conduit 11 may be adapted for connection to a further receptacle for capturing the subsequent volume, or may be adapted for connection to a further liquid sampling device, e.g. a second sampling device in accordance with embodiments described hereinabove (and suitable outlet to inlet connectors) for sampling a fraction of the subsequent volume of the liquid flow, e.g. a fraction of the mid-stream urine.

Figure 6:
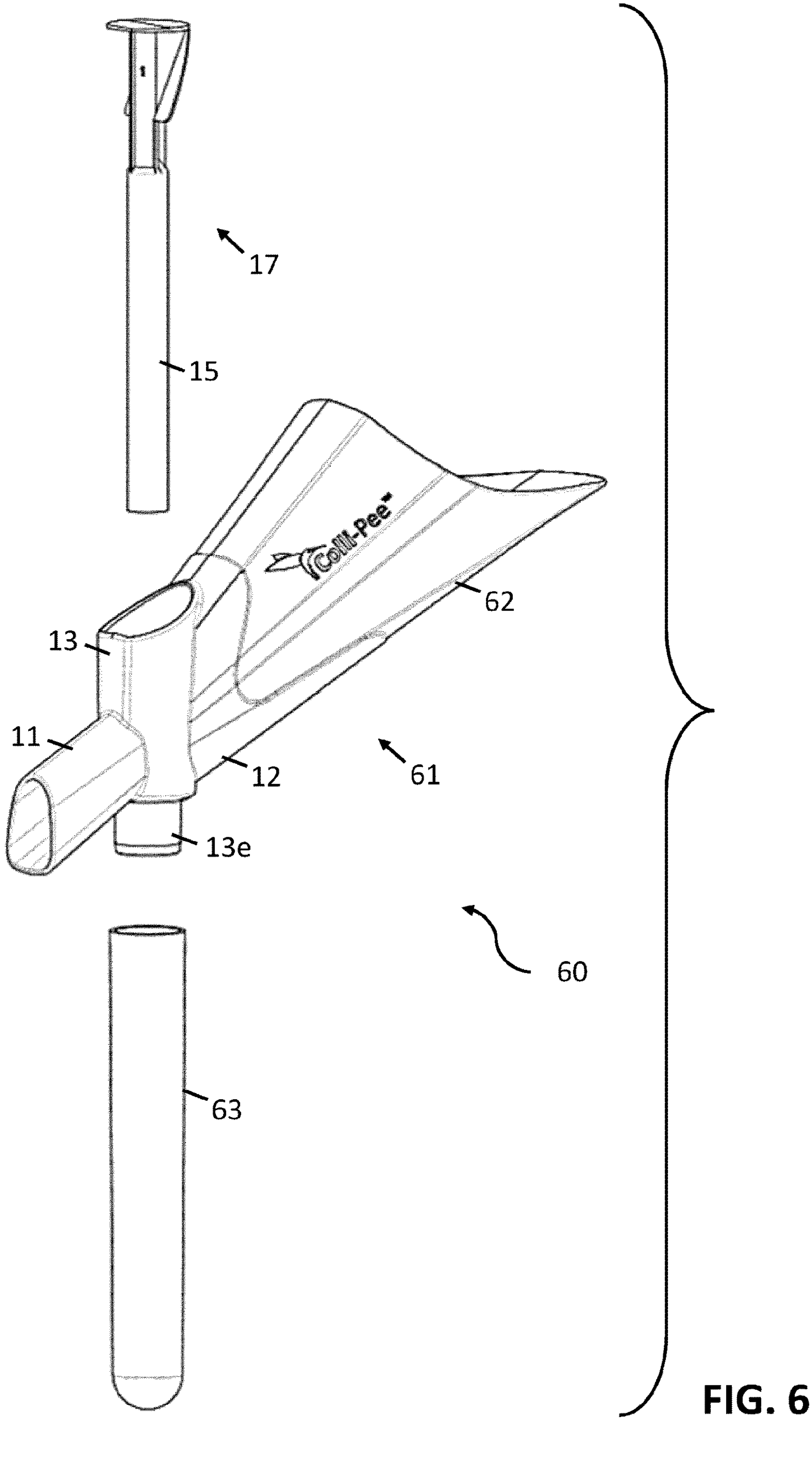
FIG. 6 is an exploded view of a kit of parts comprising a device for sampling an initial volume of a liquid flow according to an embodiment of the invention.

Components of the device 10 for sampling an initial volume of a liquid flow as described hereinabove, as well as attachable accessories, may be provided separately in a kit of parts. With reference to FIG. 6, an exploded view of such a kit 60 is shown. It is an advantage of the kit 60 that the parts can be manufactured separately before they are delivered to the user as a complete kit in a compact box (e.g. smaller than e.g. 380 mm×265 mm×32 mm, and shipped by regular mail), or as replacement parts for a previously purchased kit, who is assembling the sampling device according to instructions. The kit of parts 60 comprises the valve structure 17, the inlet conduit 12, the outlet conduit 11, the valve casing 13, and an optional receptacle 63. Preferably, the valve casing 13 and the inlet and outlet conduits 12, 11 are provided as a single integrally formed unit 61 such that both conduits 11, 12 are connected to the valve casing 13 and their proximate openings are permanently aligned with the inlet 13*a* and outlet 13*b* of the valve casing 13. A receptacle 63 (preferably with closing lid) is connectable to the valve casing 13 at a sample connector 13*e* thereof and has a collection volume equal to or larger than the initial volume of the liquid flow to be sampled, e.g. less than the first 15 ml of first-void urine, e.g. less than or equal to 4 ml of first-void urine. A dissolvable material layer of preservation agents or a buffer solution may be applied to a bottom of the receptacle 63 prior to the sampling of the initial volume. This allows preserving the sampled initial volume during the time required for sending the closed receptacle 63 to the laboratory charged with the urinalysis. Suitable materials for the components of the sampling device comprise, without being limited thereto, polypropylene, biodegradable polymers, or form-shaped bagasse, and withstand urine at body temperatures, e.g. at least 40 degree Celsius. Plastic components of the sampling device may be manufactured at large scale by injection molding. Preferably, the materials for the components of the sampling device are also easily compressed or folded such that they can be sent, as a kit or as separate parts, to the user by mail (e.g. when less than 28 mm thick), who then expands or unfolds the components for assembly. In embodiments of the invention, in which the inlet conduit 12 is not formed as a funnel 62, such an inlet conduit may be adapted to receive and secure a separate funnel at the distal opening, e.g. a funnel support may comprise a V-groove for placing and aligning a funnel and a clip for securing and maintaining an open configuration of the funnel. An accessory funnel may be part of the kit 60 and deliverable in compact form, e.g. folded or collapsed before being unfolded or expanded prior to use. A separate funnel has the advantage that it may be provided as a disposable funnel made from biodegradable polymers and suitable for direct flushing, in addition of being fitted to the anatomy of a specific gender, e.g. male or female. It is noticed that the valve structure 17 as one of the components of the kit 60 is removably insertable into the valve casing 13 at an opening at its top. In this case, the previously mentioned resilient stopper 13*d* is flexed under the pressure of the cap 16 when the valve structure 17 is being inserted. Once the cap 16 has passed the stopper 13*d* it snaps back to its original position, thus is restricting the axial movement of the inserted valve structure 17 to the interior of the valve casing 13 and prevents it from falling out. To facilitate insertion during assembly, the stopper 13*d* may have a downwards sloping upper side.

Figure 7:
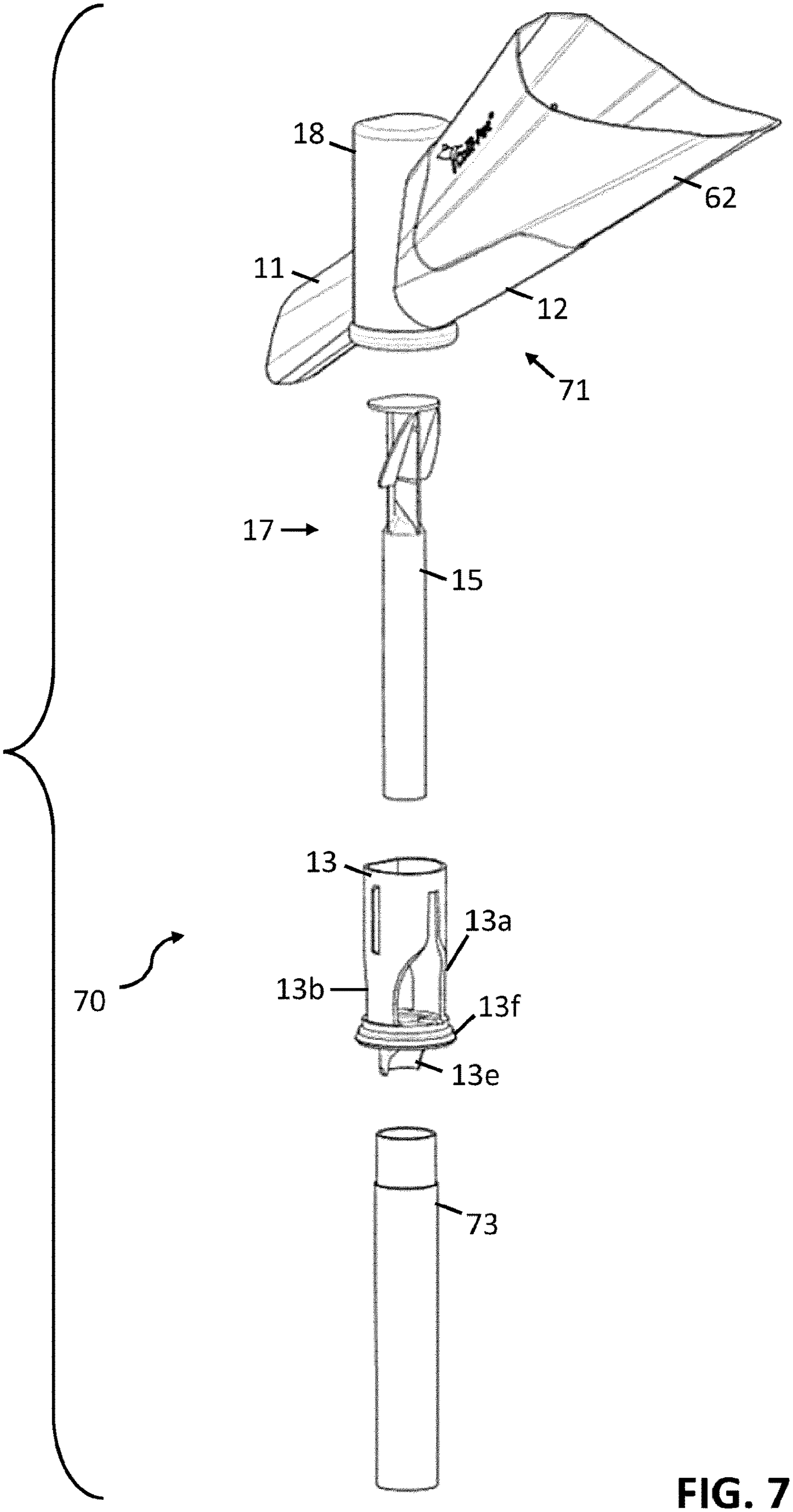
FIG. 7 is an exploded view of a kit of parts comprising a device for sampling an initial volume of a liquid flow according to a different embodiment of the invention.

A variation of the preceding embodiment is now described with reference to FIG. 7. The kit of parts 70 comprises the valve structure 17, the inlet conduit 12, the outlet conduit 11, a bonnet 18, the valve casing 13, and an optional receptacle 73. Preferably, the bonnet 18 and the inlet and outlet conduits 12, 11 are provided as a single integrally formed unit 71 such that both conduits 11, 12 are connected to the bonnet 18 and have their proximate openings formed through the bonnet sidewalls. The present embodiment is different in that the valve casing 13 now takes the form of a sleeve that is inserted into and covered by the bonnet 18. It is understood from FIG. 6 that the valve structure 17 is first inserted into the valve casing 13 before the valve casing with valve structure is inserted into the bonnet 18, or the bonnet 18 is slipped thereover. The hollow interior of the valve casing 13 for the assembled sampling device is thus delimited by the base 13*f* of the valve casing 13, the double-walled section comprising the projecting side wall of the valve casing and the bonnet side wall, and the top wall of the bonnet. In consequence, the liquid passageway between inlet and outlet 13*a*, 13*b*, is completely enclosed, providing additional protection against spillage also on the top of the valve casing. The bonnet 18 may have a flexible annulus provided at its lower end portion, which annulus snap-fits the basis 13*f* of the valve casing 13 to securely fasten these two parts together. To facilitate sliding the bonnet 18 over the valve casing 13 and to ensure correct orientation, the bonnet 18 may be provided with a similar cylindrical shape as the valve casing 13, e.g. a generalized cylinder shape with asymmetrical base, e.g. a circular segment. This also allows the inlet 13*a* to be permanently aligned with the proximate opening of the inlet conduit 12 (formed through the bonnet) and the outlet 13*b* to be permanently aligned with the proximate opening of the outlet conduit 11 (also formed through the bonnet). A receptacle 73 (preferably with closing lid) is connectable to the valve casing 13 at a sample connector 13*e* thereof and has a collection volume equal to or larger than the initial volume of the liquid flow to be sampled, e.g. less than the first 15 ml of first-void urine, e.g. less than or equal to 4 ml of first-void urine. The sampling connector 13*e* which is shown in FIG. 7 has a baffle-forming recess provided at its lower end portion. As mention before, a dissolvable material layer of preservation agents or a buffer solution may be applied to a bottom of the receptacle 73 prior to the sampling of the initial volume.

The following describes a best mode of operating the device for sampling an initial volume of a liquid flow according to embodiments of the invention. To detect sexually transmitted infections in urine samples, samples taken from of a first small fraction of first-void urine, e.g. the initial 4 ml thereof, are recommended; this improves the reliability of the results obtained by urinalysis. Therefore, care has to be taken to not spill or lose any of the initial volume during the process of taking samples. This should not come at the expense of less handling comfort and hygiene when using the sampling device. Prior to sampling the initial volume of the liquid, e.g. urine, the user of the sampling device is connecting the receptacle to the valve casing (e.g. by screwing, snap-fitting, push-fitting the receptacle onto a sampling connector), or, if the receptacle has been previously connected to the valve casing, may check that it is connected in a secure way, e.g. such that it cannot loosen and fall down subsequently. In cases, in which the sampling device is delivered to the user as a kit of parts, optionally including further parts such as expandable funnels, the user is prompted to assemble these parts as described hereinabove. A buffer solution or perseveration agent may be added to the bottom of the receptacle. The user then positions the distant opening 12*a* of the inlet conduit 12 on the urinary meatus, wherein the wide funnel-shaped opening 12*a* is adapted to the anatomical shape around the meatus to prevent spillage or losses during the time urine is being execrated by the user's body and received by the inlet conduit 12. At the same time, the user is positioning the distant opening 11*a* of the outlet conduit 11 over or into a further recipient, e.g. into a larger container or a toilet. Next the user verifies that the sampling device is oriented nearly vertically and starts the urination process. An initial volume of first-void urine to the sampling device, where it is received by the inlet 13*a* and directed through the sampling outlet 13*c* into the receptacle. While receiving the initial volume, the lifting member 15*a* forces the valve structure 17 upwards until the cap 16 is pushing against the stopper 13*d*, e.g. until the valve structure has been moved from the sampling position to the diverting position. At that moment in time, the initial volume of urine has been sampled and the sample outlet 13*c* is being obstructed by the lower portion of the stem 15. However, the thinner portion of the stem permits the subsequent volume of urine to flow through the passageway in the valve casing 13 towards the outlet 13*b* and the distant opening of the outlet conduit 11*a*, where it is expelled from the sampling device. Once the urination is completed and no more urine is entering the inlet conduit 12, the user loosens the receptacle with the sampled initial volume. A closing lid can be firmly screwed or snapped onto the receptacle for safe delivery of the urine sample to the laboratory charged with the urinalysis and the detection of pathogens. The user may further dispose of the sampling device, e.g. by flushing a biodegradable device in the toilet, or may wash or rinse and disinfect the sampling device for a next use (optionally replacing accessories such as funnels).

While the invention has been illustrated and described in detail in the drawings and foregoing description, such illustration and description are to be considered illustrative or exemplary and not restrictive. The foregoing description details certain embodiments of the invention. It will be appreciated, however, that no matter how detailed the foregoing appears in text, the invention may be practiced in many ways. The invention is not limited to the disclosed embodiments. Other variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A device for sampling an initial volume of a liquid flow, comprising:

an inlet conduit for receiving the liquid flow, an outlet conduit for draining a subsequent volume of the liquid flow, a valve casing arranged between the inlet conduit and the outlet conduit and having a passageway formed therethrough to fluidly connect the inlet conduit to the outlet conduit, a sample outlet for draining the initial volume of the liquid flow extending through the valve casing and into said passageway, a valve structure arranged for axial movement in the valve casing traverse to a direction of liquid flow through the passageway, the valve structure comprising a gate for obstructing the passageway and preventing the initial volume of the liquid flow from being transferred to the outlet conduit when the valve structure is in a sampling position, and the valve structure further comprising a stem connected to the gate and adapted for obstructing the sample outlet without obstructing the passageway when the valve structure is in a diverting position, at least one elongated groove being formed in a surface of the gate facing the inlet conduit and the at least one elongated groove extending from the gate to the stem, said at least one elongated groove being adapted for receiving the initial volume of the liquid flow and for guiding said initial volume along the gate, the stem, and through the sample outlet towards a receptacle, connectable to the valve casing, when the valve structure is in the sampling position, a lifting member connected to the stem for moving the valve structure from the sampling position to the diverting position while the initial volume of the liquid flow is being sampled through the sample outlet.

2. The device according to claim 1, wherein the lifting member comprises an air cavity formed in a lower portion of the stem.

3. The device according to claim 1, wherein the gate comprises a slanted wall with edges lying flush with inner surfaces of the valve casing when the valve structure is in the sampling position.

4. The device according to claim 1, wherein the stem is comprising a thinned upper portion, a wider lower portion, and a transition segment connected between the thinned upper portion and the wider lower portion for tapering the thinned upper portion to the wider lower portion, the at least one elongated groove extending into the thinned upper portion of the stem and an outer surface of the wider lower portion of the stem lying flush with a bore of the sample outlet when the valve structure is in the diverting position.

5. The device according to claim 4, wherein ribbed edges are protruding from an outer surface of the thinned upper portion of the stem, the ribbed edges being in a telescoping relationship with the bore of the sample outlet.

6. The device according to claim 1, wherein the valve casing further comprises a sampling connector connected to a base of said valve casing and at least partially circumferentially enclosing the sample outlet formed through said base.

7. The device according to claim 6, wherein the sampling connector comprises an angled or baffle-forming opening at a lower end portion thereof, opposite to the base.

8. The device according to claim 1, wherein the valve structure further comprises a cap connected to the gate, a rim of the cap lying flush and being in a telescoping relationship with an inner surface of the valve casing.

9. The device according to claim 8, wherein the rim of the cap and the inner surface of the valve casing have a mating asymmetrical shape for preventing a rotational movement of the valve structure relative to the valve casing.

10. The device according to claim 1, wherein the valve casing comprises a resilient stopper protruding from an inner surface of said valve casing and positioned to cooperate with an upper edge of the valve structure such that a farther axial movement of the valve structure is limited when the upper edge of the valve structure is pushing against the resilient stopper in the diverting position.

11. The device according to claim 1, wherein the at least one elongated groove is separated into two grooves by a stabilizing wall.

12. The device according to claim 1, wherein the inlet conduit, outlet conduit, and the valve casing are monolithically formed as a single part, proximate openings of the inlet conduit and the outlet conduit being respectively aligned with an inlet and an outlet of the passageway through the valve casing.

13. The device according to claim 1, further comprising a bonnet connected between the inlet conduit and the outlet conduit and forming a lid to the valve casing, the bonnet having proximate openings of the inlet conduit and outlet conduit formed therethrough, and the bonnet being secured to a base of the valve casing such that proximate openings of the inlet conduit and the outlet conduit are respectively aligned with an inlet and an outlet of the passageway through the valve casing.

14. A kit of parts, comprising:

a bonnet having at least three openings, an inlet conduit connectable to a first opening of the bonnet, an outlet conduit connectable to a second opening of the bonnet, a valve casing removably insertable into the bonnet via a third opening therein, a base of the valve casing being connectable to the third opening, the valve casing having an inlet and an outlet formed therethrough defining a liquid passageway though the valve casing, a sample outlet extending through the base of the valve casing and into the passageway, the valve casing having an opening provided at a top side thereof, opposite to the base, a valve structure removably insertable into the valve casing, the valve structure being arranged for axial movement in the valve casing, traverse to a direction of liquid flow through the passageway, the valve structure comprising a gate for obstructing the passageway when the valve structure is in a sampling position, and the valve structure further comprising a stem connected to the gate and adapted for obstructing the sample outlet without obstructing the passageway when the valve structure is in a diverting position, at least one elongated groove being formed in a surface of the gate and the at least one elongated groove extending from the gate into the stem, a lifting member connectable to the stem.

15. A kit according to claim 14, wherein the inlet conduit, outlet conduit, and the bonnet are provided as a monolithic part.

16. A kit according to claim 14, further comprising one or more of the following characteristics:

a) the lifting member and the stem of the valve structure are provided as a monolithic part and the lifting member comprises an air cavity;

b) the gate comprises a slanted wall with edges fitted to inner surfaces of the valve casing;

c) the valve structure further comprises a cap connected to the gate, a rim of the cap being fitted to an inner surface of the valve casing to establish a telescoping relationship therewith;

d) the valve casing comprises a resilient stopper protruding from an inner surface of said valve casing and positioned to cooperate with an upper edge of the valve structure such that a farther axial movement of the valve structure is limited when the upper edge of the valve structure is pushing against the resilient stopper in the diverting position;

e) the kit further comprises a receptable with a volume ranging between 1 ml and 50 ml, the receptacle being connectable to a sampling connector provided at a lower side of the base of the valve casing;

f) the kit further comprises a funnel connectable to the inlet conduit, the inlet conduit being adapted for receiving and securing the funnel;

g) the inlet conduit has a flexible shape; and h) one or more parts of the kit are made from biodegradable polymers.

17. A kit according to claim 14, wherein said at least one elongated groove is adapted for, when the kit of parts is assembled and in use, receiving an initial volume of a liquid flow and guiding said initial volume along the gate, the stem, and through the sample outlet towards a receptacle, connectable to the valve casing, when the valve structure is in the sampling position.

18. A kit of parts, comprising:

a valve casing having an inlet and an outlet formed therethrough defining a liquid passageway though the valve casing, a sample outlet extending through a base of the valve casing and into the passageway, the valve casing having an opening provided at a top side thereof, opposite to the base, an inlet conduit connectable to the inlet of the valve casing, an outlet conduit connectable to the outlet of the valve casing, a valve structure removably insertable into the valve casing, the valve structure being arranged for axial movement in the valve casing, traverse to a direction of liquid flow through the passageway, the valve structure comprising a gate for obstructing the passageway when the valve structure is in a sampling position, and the valve structure further comprising a stem connected to the gate and adapted for obstructing the sample outlet without obstructing the passageway when the valve structure is in a diverting position, at least one elongated groove being formed in a surface of the gate and the at least one elongated groove extending from the gate into the stem, said at least one elongated groove being adapted for, when the kit of parts is assembled and in use, receiving an initial volume of a liquid flow and guiding said initial volume along the gate, the stem, and through the sample outlet towards a receptacle, connectable to the valve casing, when the valve structure is in the sampling position, a lifting member connectable to the stem.

19. A kit according to claim 18, wherein the inlet conduit, outlet conduit, and the valve casing are provided as a monolithic part.

20. A kit according to claim 18, further comprising one or more of the following characteristics:

(a) the lifting member and the stem of the valve structure are provided as a monolithic part and the lifting member comprises an air cavity;

(b) the gate comprises a slanted wall with edges fitted to inner surfaces of the valve casing;

(c) the valve structure further comprises a cap connected to the gate, a rim of the cap being fitted to an inner surface of the valve casing to establish a telescoping relationship therewith;

(d) the valve casing comprises a resilient stopper protruding from an inner surface of said valve casing and positioned to cooperate with an upper edge of the valve structure such that a farther axial movement of the valve structure is limited when the upper edge of the valve structure is pushing against the resilient stopper in the diverting position;

(e) the kit further comprises a receptacle with a volume ranging between 1 ml and 50 ml, the receptacle being connectable to a sampling connector provided at a lower side of the base of the valve casing-base;

(f) the kit further comprises a funnel connectable to the inlet conduit, the inlet conduit being adapted for receiving and securing the funnel;

(g) the inlet conduit has a flexible shape; and (h) one or more parts of the kit are made from biodegradable polymers.

* * * * *